United States Patent [19]

Knollmueller

[11] 4,198,346

[45] Apr. 15, 1980

[54] PREPARATION OF TRIALKOXYSILANOLS

[75] Inventor: Karl O. Knollmueller, Hamden, Conn.

[73] Assignee: Olin Corporation, New Haven, Conn.

[21] Appl. No.: 44,828

[22] Filed: Jun. 1, 1979

[51] Int. Cl.² ............................................. C07F 7/04
[52] U.S. Cl. .................................... 556/463; 556/451; 556/458
[58] Field of Search ................................. 260/448.8 A

[56] References Cited

U.S. PATENT DOCUMENTS

| | | | |
|---|---|---|---|
| 2,727,054 | 12/1955 | Wright | 260/448.8 A |
| 2,758,127 | 8/1956 | Goldschmidt et al. | 260/448.8 A |
| 3,965,135 | 6/1976 | Knollmueller | 260/448.8 A |
| 3,965,136 | 6/1976 | Knollmueller | 260/448.8 A |
| 4,077,993 | 3/1978 | Knollmueller | 260/448.8 A X |

Primary Examiner—Paul F. Shaver
Attorney, Agent, or Firm—William A. Simons; Thomas P. O'Day

[57] ABSTRACT

An improved method is disclosed for the preparation of trialkoxysilanols. The process involves hydrolysis of corresponding trialkoxyhalosilanes with solid bicarbonate in the presence of a critical catalytic amount of water.

12 Claims, No Drawings

PREPARATION OF TRIALKOXYSILANOLS

Silicate esters, long appreciated as a class of compounds, only recently have been extensively investigated and recognized as exhibiting physical properties which indicate superior potential utility as synthetic lubricants and functional fluids. One major obstacle for such application, however, has been their hydrolytic instability.

Novel silicate ester compounds now have been developed which overcome the drawback of hydrolytic instability, and, in turn, continue to feature highly favorable physical properties. Such novel compounds, characterized as alkoxysilane cluster compounds, and their preparation are described in the present inventor's commonly assigned U.S. Pat. Nos. 3,965,136, 3,992,429 and 4,058,546, the disclosures of which are hereby incorporated by reference in their entireties.

The synthesis of each of the respective alkoxysilane cluster compounds involves the use of sterically hindered trialkoxysilanols as starting materials. These trialkoxysilanols have the general formula:

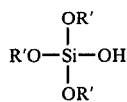

$$\text{R'O}-\underset{\underset{\text{OR'}}{|}}{\overset{\overset{\text{OR'}}{|}}{\text{Si}}}-\text{OH} \qquad \text{I}$$

wherein R' is independently selected from hydrogen, alkyl, alkenyl, aryl, or aralkyl, with the proviso that at least a majority of the pendant R' groups attached to the central Si atom are sterically hindered alkyl groups having at least 3 carbon atoms. It is desirable that R' be selected from hydrogen, alkyl or alkenyl having from about 1 to about 18 carbon atoms or aryl or aralkyl having about 6 to about 24 carbon atoms, preferably, R' is slected from hydrogen, alkyl or alkenyl having about 1 to about 8 carbon atoms, or aryl or aralkyl having about 6 to about 14 carbon atoms, subject to the preceding proviso. The majority of the R' groups are sterically hindered alkyl groups having about 3 to about 24 carbon atoms; preferably the majority of the R' groups are sterically hindered alkyl groups having about 4 to about 12 carbon atoms. In the most preferred embodiment, all of the R' groups are sterically hindered alkyl groups. The term "sterically hindered alkyl groups" is meant to be defined as alkyl radicals which contribute to the hydrolytic stability of the molecule, i.e., which inhibit the reaction of water with the silicon-oxygen or the carbon-oxygen bonds in the molecule. Exemplary of sterically hindered alkyl radicals are non-linear primary alkyl radicals having a beta position side chain of at least 2 carbon atoms, secondary alkyl radicals and tertiary alkyl radicals. Particularly preferred sterically hindered alkyl groups include sec. butyl, isobutyl, 2-ethyl butyl, 2-ethyl pentyl, 3-ethyl pentyl, 2-ethyl hexyl, 3-ethyl hexyl, 2,4-dimethyl-3-pentyl, etc. Sec. butyl groups are most preferred.

Silanols generally are prepared by a hydrolysis reaction from their corresponding chlorosilanes in the presence of a hydrogen halide acceptor base compound. The acceptor may be any compound which will accept hydrogen halide and thereby promote the formation of the silanol compounds pursuant to Equation (A) shown below:

$$R_3Si-Cl + H_2O + B \rightarrow R_3Si-OH + B \cdot HCl \qquad (A)$$

wherein R, for example, is an alkyl group and B is the base compound.

Due to their instability, however, silanols including trialkoxysilanols, generally are difficult to prepare and isolate, and often require specially adapted techniques for each type of respective silanol product. For example, trialkoxysilanols having primary lower alkyl groups tend to form condensation products. The silanol self-condenses to form disiloxane with the elimination of water, $$2(R'O)_3Si-OH \rightarrow (R'O)_3Si-O-Si(OR')_3 + H_2O, \qquad (B)$$

and also condenses with unreacted halosilane starting material, $$(R'O)_3Si-OH + Cl-Si(OR')_3 + B \rightarrow B \cdot HCl + (R'O)_3Si-O-Si(OR')_3. \qquad (C)$$

Such side reactions lower yields and may even make independent existence of the silanol nearly impossible.

The trialkoxysilanols which are the subject of the presently invented process contain sterically hindered alkyl groups, as defined above, which significantly enhance silanol stability. According to U.S. Pat. No. 2,727,054, these silanols, represented by tri-sec-butoxysilanol, can be prepared by first converting a trialkoxyhalosilane to an amide through reaction with ammonia, and then hydrolyzing the amide to the corresponding silanol. These reactions can be outlined as follows:

$$(R'O)_3Si-Cl + 2NH_3 \xrightarrow{\text{heptane}} NH_4Cl + (R'O)_3Si-NH_2 \qquad (D)$$

$$(R'O)_3Si-NH_2 + H_2O \xrightarrow{\text{heptane}} NH_3 + (R'O)_3Si-OH. \qquad (E)$$

While this reaction scheme is reasonably productive, it is beset by the drawbacks that condensation products, such as disiloxanes, lower yields, and some amide survives the hydrolysis to contaminate the product silanol.

A particularly favorable synthesis procedure to prepare sterically hindered trialkoxysilanol compounds, now has been discovered, according to the present invention. The discovered process involves the reaction of a trialkoxyhalosilane with solid bicarbonate, preferably, NaHCO$_3$, in the presence of a critical catalytic amount of water, as represented by the following equation:

$$(R'O)_3Si-X + NaHCO_3 \xrightarrow[\text{water}]{\text{solvent}} \qquad (F)$$

$$NaCl + CO_2 \uparrow + (R'O)_3Si-OH$$

wherein X is a halogen, preferably chlorine, and R' is defined as above. Such a reaction has been found to offer excellent yields; and, the purity of the product silanol compound further accomodates storage stability. As Equation (F) suggests, the reaction preferably is carried out in a solvent. While the solvent is not strictly necessary, it does serve to moderate the rate of reaction and thereby to enhance the separation of the unreacted NaHCO$_3$ and by-product NaCl from the trialkoxysilanol compound product. The solvent used may be any polar, non-protonic solvent which dissolves the reactants and does not interfere with the reaction.

Among the solvents which may be used are ethers such as diethyl ether, dibutyl ether, tetrahydrofuran, and the like. Generally, the weight ratio of trialkoxyhalosilane to solvent ranges from about 1:1 to about 1:5; about 1:2.2 to about 1:3.2 is preferred; most preferred is a range of about 1:2.4 to about 1:2.8. Too low a solvent level favors undesirable side reactions; too high a solvent level retards reaction speed and, in addition, entails unnecessary solvent handling on work up.

Bicarbonate generally does not require the presence of water to effect hydrolysis. However, it unexpectedly has been discovered that the presence of a critical catalytic amount of water is necessary to obtain high product yield and purity. Accordingly, about 0.1 to about 1.0 weight percent of water is added to the reaction, based on the weight of the solvent before the addition of bicarbonate. Preferably, about 0.2 to about 0.4 percent is used; the most preferred range is about 0.25 to about 0.38 percent. Increasing water levels tend to favor formation of by-products and may even lead to "cloudiness" in the resulting product. However, the solubility of the water in the particular chosen solvent also exerts an effect on the amount of water that can be used. For example, using a solvent such as diethyl ether, featuring a low solubility for water, permits water levels of up to about 0.8 percent without beginning to induce impurity formation.

Theoretically, a 1:1 molar ratio of trialkoxyhalosilane to bicarbonate is needed. However, the bicarbonate generally is used in a molar excess amount ranging from about 1.3 to about 4.0 moles per mole of trialkoxyhalosilane. A molar excess ranging from about 2.0 to about 3.0 moles per mole of trialkoxyhalosilane is preferred, with a range of about 2.2 to about 2.4 moles $NaHCO_3$ being most preferred.

The reaction temperature generally may range from about 0° to about 80° C. with a temperature range of about 20° to about 40° C. being preferred. Most preferably, the temperature of the reaction is about 25° to about 30° C.

After the reaction of the trialkoxyhalosilane with the bicarbonate has proceeded to completion, the by-product NaCl and excess $NaHCO_3$ are separated by filtration. The solvent then can be removed using standard distillation techniques.

The sterically hindered trialkoxysilanols prepared according to the present invention have particular utility as reactants in the preparation of alkoxysilane cluster compounds. To prepare such cluster compounds, for example, the prepared trialkoxysilanols are reacted with a substituted trihalosilane in the presence of an acceptor base in a solvent reaction medium. Such a procedure is more fully described in the present inventor's U.S. Pat. Nos. 3,965,136 and 4,077,993, the disclosures of which hereby are incorporated in their entireties by reference. A typical alkoxysilane cluster synthesis can be represented by the following equation:

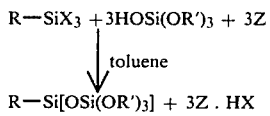

wherein X represents halogen groups; R is hydrogen, an alkyl, alkenyl, aryl or aralkyl; each R' is independently selected from the same group as R with the proviso that at least a majority of R' radicals are sterically hindered alkyl groups having at least 3 carbon atoms; and Z is a hydrogen halide acceptor base.

The following examples depict various embodiments of the present invention; they are intended to be illustrative rather than limiting in nature. All parts and percentages are by weight unless otherwise specified.

Preparation of Tri-Sec-Butoxysilanol

Example I

A two liter three neck flask equipped with a stirrer, reflux condenser and an equilibrated dropping funnel was charged with 700 ml diethyl ether (500.5 g) 120 g $NaHCO_3$ (1.428 moles) and 4 ml $H_2O$ catalyst (0.8% by weight solvent). During a period of 2 hours, 178.5 g (sec. $C_4H_9O)_3$ SiCl (0.631 moles) was added through the equilibrated dropping funel. The off-gases ($CO_2$ and some entrained diethyl ether) were monitored by passing through a flow meter connected to the outlet of the reflux condenser. Ten minutes after the addition was completed, the $CO_2$ evolution ceased. The mixture was stirred for 1 hour more, then 10 g anhydrous $MgSO_4$ was added to bind any water. After stirring for 2 hours the solids were filtered and washed with 100 ml diethyl ether. The combined filtrate and wash was concentrated by distilling off the ether; the last traces of ether were removed on a rotary evaporator at 12 m Hg/40° C. The yield of product silanol was 164.4 g or 98.5% of theory.

Example II

In this Example, the reaction equipment used was similar to that in Example I, but larger. 1041 g $NaHCO_3$ (12.391 moles) was slurried in three liters THF (2660 g). 6.6 g water was added as catalyst (0.25% by weight solvent). 1041 g (sec. $C_4H_9O)_3$ SiCl (3.679 moles) was dropped into the reaction mixture within 3 hours and post reacted 30 minutes. 25 g $MgSO_4$ was added to bind the water. The filtered product was stripped from solvent on a rotary evaporator. 932.5 g product silanol of 97.8% purity was obtained which is a 93.6% yield.

Example III

A 300 Gal. reactor (Glass lined Pfaudler Reactor) was charged with 190 Gal. THF (719.2 l or 637.9 kg) and 450 lbs $NaHCO_3$ (209.11 kg, 2.429 kg mole). Five pounds of water*(2.26 kg or 0.355% by weight solvent) was added as a catalyst. To the stirred reactor, 640 pounds chlorosilane ClSi $(OC_4H_9 sec)_3$ (290.3 kg 1.026 kg -mole) was metered in during 6 hours and post reacted 2 hours. To bind the water catalyst, 35 pounds $MgSO_4$ (15.87 kg) was added and the contents stirred for 8 hours. The solids were filtered and washed with ∼50 Gal. THF. The filtrate was transferred into a distillation unit and the solvent distilled through a 10 foot distillation column packed with Berle saddles. The pot temperature was not allowed to go above 80° C. Last traces solvent were removed at reduced pressure. The material purity ranged from 95 to 97% while yields ranged from 90 to 94%.

*The $MgSO_4$ does not take up all water; recycled THF is subsequent runs was analyzed and the water content adjusted to be 0.35% by weight of solvent.

What is claimed is:

1. A process for the preparation of sterically hindered trialkoxysilanol compounds of the formula:

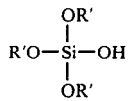

wherein R' is independently selected from hydrogen, alkyl, alenyl, aryl, or aralkyl, with the proviso that at least a majority of the pendant R' groups attached to the central Si atom are sterically hindered alkyl groups having at least 3 carbon atoms, comprising reacting a corresponding trialkoxyhalosilane of the formula, (R'O)$_3$SiX, wherein X is a halogen and R' is defined as above, with solid bicarbonate is a polar non-protonic solvent medium in the presence of a catalytic amount of water.

2. The process of claim 1 wherein said bicarbonate is NaHCO$_3$.

3. The process of claim 2 wherein the bicarbonate is used in an amount ranging from about 1.3 to about 4 moles per mole of trialkoxyhalosilane.

4. The process of claim 3 wherein the bicarbonate is used in an amount ranging from about 2.0 to about 3.0 moles per mole of trialkoxyhalosilane.

5. The process of claim 4 wherein the bicarbonate is used in an amount ranging from about 2.2 to about 2.4 moles per mole of trialkoxyhalosilane.

6. The process of claim 1 wherein the catalytic amount of water ranges from about 0.1 to about 1.0 percent. by weight based on the weight of solvent prior to the addition of bicarbonate.

7. The process of claim 6 wherein the water ranges in amount from about 0.2 to about 0.4 percent.

8. The process of claim 7 wherein the water ranges in amount from about 0.25 to about 0.28 percent.

9. The process of claim 1 wherein the solvent is an ether.

10. The process of claim 9 wherein the solvent is selected from the group consisting of diethyl ether, dibutyl ether, tetrahydrofuran, and mixtures thereof.

11. The process of claim 10 wherein the solvent is tetrahydrofuran.

12. The process of claim 7 wherein tributoxychlorosilane is reacted with solid NaHCO$_3$ in a tetrahydrofuran medium.

* * * * *